(12) United States Patent
Heinze et al.

(10) Patent No.: US 7,175,346 B2
(45) Date of Patent: Feb. 13, 2007

(54) MOTORIZED ADJUSTABLE X-RAY APPARATUS

(75) Inventors: Udo Heinze, Erlangen (DE); Peter Nögel, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/965,388

(22) Filed: Oct. 14, 2004

(65) Prior Publication Data

US 2005/0117710 A1    Jun. 2, 2005

(30) Foreign Application Priority Data

Oct. 14, 2003    (DE) ............................... 103 47 733

(51) Int. Cl.
*H05G 1/02* (2006.01)
*H05G 1/56* (2006.01)

(52) U.S. Cl. ...................................... 378/197; 378/114

(58) Field of Classification Search ................ 378/196, 378/197, 198, 114, 115
See application file for complete search history.

(56) References Cited

U.S. PATENT DOCUMENTS

| | | | |
|---|---|---|---|
| 4,298,308 A * | 11/1981 | Richter ........................ 700/260 |
| 4,448,200 A * | 5/1984 | Brooks et al. ................. 378/20 |
| 5,105,455 A * | 4/1992 | Kato et al. .................... 378/117 |
| 5,878,112 A | 3/1999 | Koertge | |
| 6,409,381 B1 | 6/2002 | Siebenhaar et al. | |
| 6,869,217 B2 * | 3/2005 | Rasche et al. ............... 378/197 |
| 2003/0068011 A1* | 4/2003 | Johnson et al. ............. 378/115 |
| 2003/0091156 A1* | 5/2003 | Crain et al. .................. 378/197 |

FOREIGN PATENT DOCUMENTS

| CH | 197 996 | 5/1938 |
|---|---|---|
| DE | 41 32 117 | 4/1993 |
| DE | 42 37 013 | 10/1996 |
| DE | 198 54 470 | 5/1999 |

* cited by examiner

*Primary Examiner*—Edward J. Glick
*Assistant Examiner*—Chih-Cheng Glen Kao
(74) *Attorney, Agent, or Firm*—Schiff Hardin LLP

(57) ABSTRACT

A motorized adjustable x-ray apparatus has a transmitter operable by AN operator for adjustment of a C-arm and mechanically connected with the C-arm. The transmitter allows adjustment of both an angulation angle and an orbital angle of the C-arm. The speed of the adjustment movement of the C-arm can be selected by actuation of the transmitter.

5 Claims, 2 Drawing Sheets

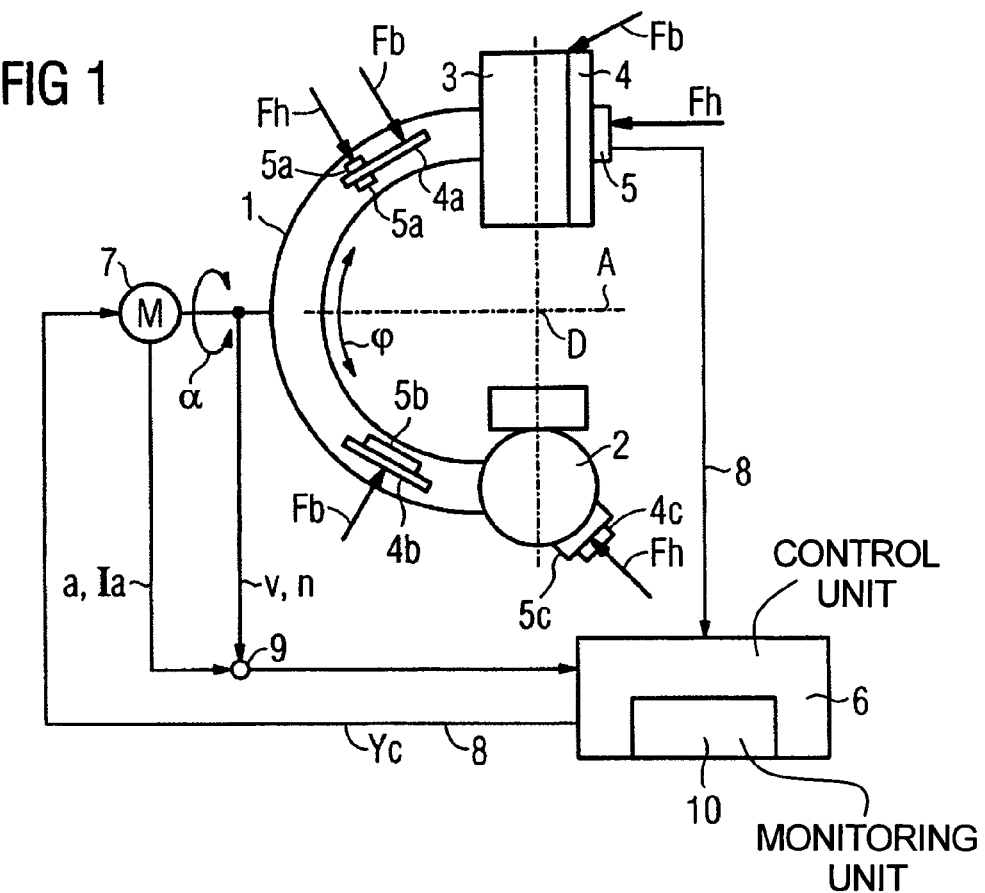
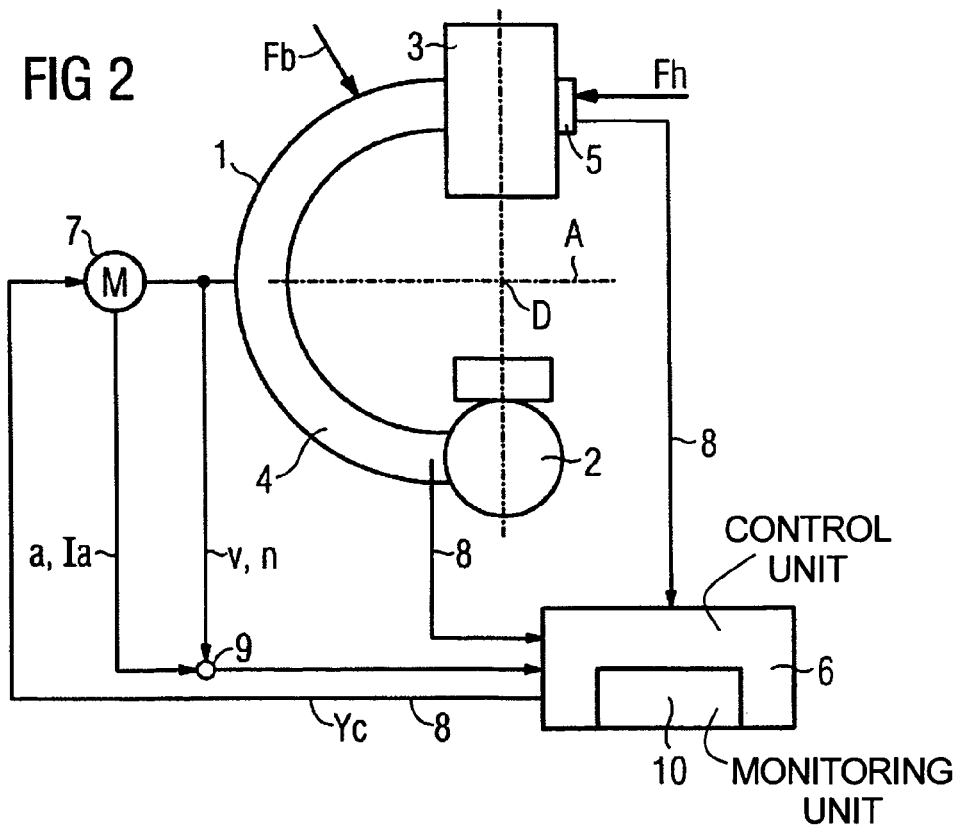

MOTORIZED ADJUSTABLE X-RAY APPARATUS

BACKGROUND OF THE INVENTION

1. Field of the Invention

The present invention concerns a motorized adjustable x-ray apparatus of the type having a C-arm, and a transmitter to be activated by the operator for adjustment of the C-arm.

2. Description of the Prior Art

An x-ray apparatus of the above general type is known, for example, from German OS 199 57 330. The x-ray apparatus known from German OS 199 57 330 has an apparatus controller in the form of an operating handle. The C-arm of the x-ray apparatus can be adjusted in the angular and orbital direction with the aid of the operating handle.

An x-ray system with adjustable components, namely a C-arm as well as a positioning table for a patient, is known from German OS 196 25 409. Collisions given adjustment movements are prevented with the aid of a computer.

A computed tomography fluoroscopy system in which commands and parameters can be entered via a console is known from German OS 198 54 470. Adjustment movements that can be triggered by the operator can be combined with a deadman's control.

An x-ray diagnostic apparatus is known from German OS 41 32 117 that has sensors that can detect proximity, contact and/or pressure with spatial resolution. In particular, a resistive foil or a capacitive circuit can be used.

C-arm x-ray apparatuses typically have moving parts with a heavy weight. To ease the operation of an x-ray apparatus, it is known, for example, from Swiss Patent 197 966 to employ an electromotor whose to provide assistance to partially compensate the weight of at least one moving part. In a design known from German OS 42 37 013, a C-arm x-ray apparatus has an electromotor as an actuator in a control loop, and a transmitter operated by the operator is provided as a reference-value transmitter and the force applied by the operator is the command variable. The control variable is in this case an acceleration of the x-ray apparatus. In this manner, the operator should receive the impression that the operator is moving a component of the x-ray apparatus with a significantly smaller mass or moment of inertia. The supporting force in the supporting mode thus is smaller than the friction force.

SUMMARY OF THE INVENTION

An object of the present invention is to further increase the operating comfort of a motorized adjustable C-arm x-ray apparatus.

This object is inventively achieved by an x-ray apparatus having a motorized adjustable C-arm, and a transmitter operable by an operator is for adjustment of the C-arm. The transmitter is provided for the adjustment of both the angulation angle and the orbital angle of the C-arm. The user is able to actuate the transmitter in a manner allowing the operator to intuitively operate the C-arm, meaning to control arbitrary movements in the circumferential direction (orbital movements) and perpendicular thereto (angulation direction). The transmitter preferably embodies sensors or acts together with sensors that enable a tactile or sensory feeling for the movement of the C-arm in the operation thereof. Force or displacement transducers of the transmitter can operate capacitively, inductively, piezoelectrically or according to other principles. In any case, the direction in which the C-arm should be moved is determined from the direction information acquired by the transmitter. The speed with which the C-arm should be moved is determined from force and angle information acquired from the transmitter. Corresponding reference values are used for speed regulation. Thus the speed of the movement of the C-arm can be predetermined by operation of the transmitter.

According to one preferred embodiment, the transmitter is fashioned as a type of rail mounted on the C-arm or on a part mechanically connected thereto, for example an image acquisition system. This is preferably shaped similar to a conventional handgrip. A single, intuitively operable operating element is thus sufficient to control all possible movements of the C-arm. A number of identical operating elements can be arranged on the C-arm and/or on an image acquisition system or x-ray radiator mounted thereto, ands any of these operating elements, i.e. an arbitrary transmitter, can be used for adjustment of the C-arm.

In another preferred embodiment, the transmitter is fashioned as a sensor membrane disposed on the C-arm, preferably along its entire circumference. An extensive area, in particular an annular or jacket-like surface region, of the C-arm is therewith available as a sensor surface. The operator grips the C-arm on the sensor membrane in the same manner in which he or she would grip a non-servo-supported adjustable C-arm. The servo support thus comes into effect nearly imperceptibly for the user, and the operation ensues in a familiar manner typical for an x-ray apparatus with an exclusively manual, non-motor-supported adjustable C-arm.

In another preferred embodiment, a central sensor is provided that detects forces acting in the suspension of the C-arm. If these forces are changed by mechanical action of the operator on the C-arm, this triggers the servo support in the movement of the C-arm. The entire C-arm, including all parts attached thereto, thus function together with the central sensor as a transmitter. A weight compensation of the C-arm is unnecessary, as in the aforementioned embodiment as well. The x-ray apparatus is designed overall with a lower weight.

In each of these embodiments, the sensitivity of the servo controller preferably is adjustable. For example, by alteration of the time constants of the movement, the feel of different C-arm masses can be conveyed. For example, parameters that simulate friction can be varied likewise. The possibility also exists to combine a number of types of transmitters in a single C-arm x-ray apparatus.

According to a preferred embodiment, the controller of the C-arm x-ray apparatus is linked with a dead man's switch. The probability of unintentional faulty operations is drastically reduced in this manner. In addition or as an alternative to this, a monitoring device can be provided that detects movement states of the C-arm and automatically engages the servo controller to avoid collisions or abnormalities. Such an abnormality, for example, may be an excessively high acceleration of the C-arm. Upon reaching an end position of the C-arm, deactivation of the motorized drive is provided.

An advantage of the invention is in that, by means of a multidimensional detection of the force applied by the operator for the adjustment of a C-arm of an x-ray apparatus, the operation of the x-ray apparatus substantially corresponds to the operation of a conventional C-arm x-ray apparatus without servo support, despite the motorized actuation.

DESCRIPTION OF THE DRAWINGS

FIG. 1 is a schematic illustration of a first exemplary embodiment of a C-arm x-ray apparatus.

FIG. 2 is a schematic illustration of a second exemplary embodiment of a C-arm x-ray apparatus.

DESCRIPTION OF THE PREFERRED EMBODIMENTS

Figure 3:
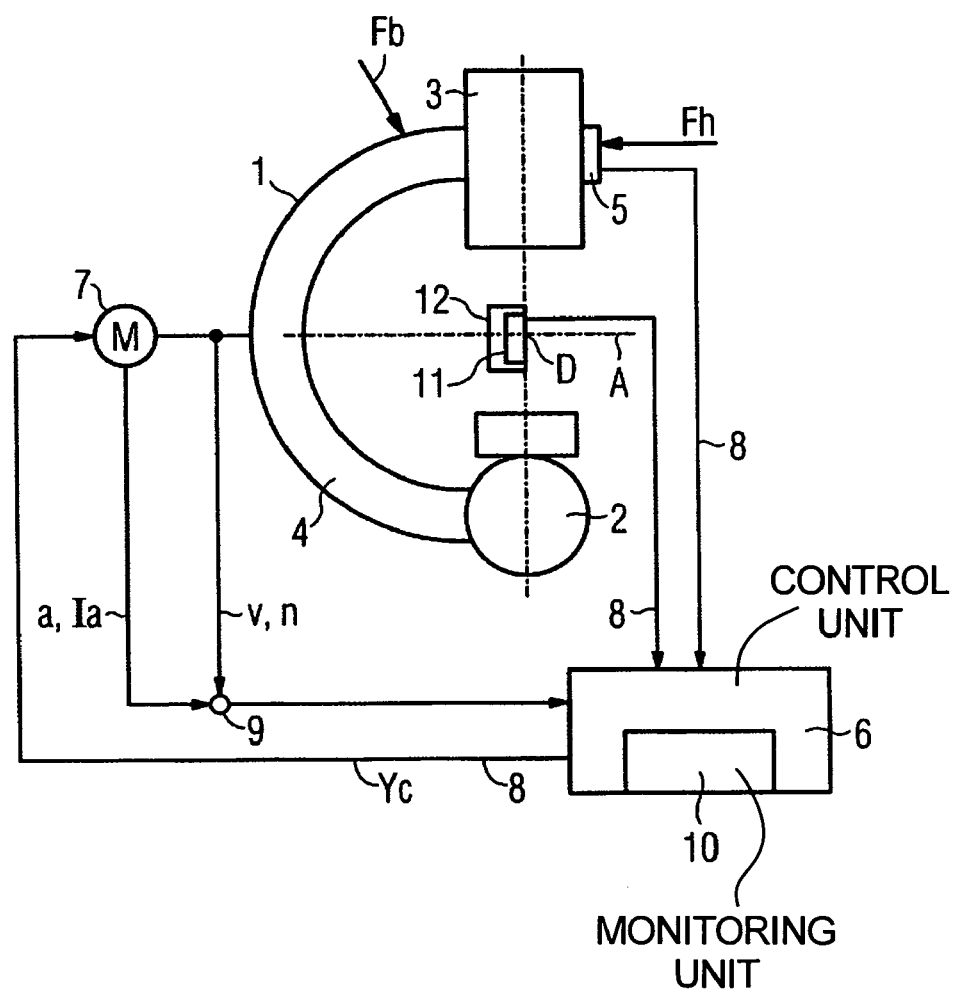
FIG. 3 is a schematic illustration of a third exemplary embodiment of a C-arm x-ray apparatus.

An x-ray apparatus with a C-arm 1, an x-ray radiator 2 mounted at one end thereof and an image acquisition system 3 mounted at the other end is shown in FIG. 1 through 3. In each exemplary embodiment, at least one transmitter 4, 4a, 4b, 4c for servo-supported adjustment of the C-arm 1 is provided in different forms. The operating force to be applied by the user is designated Fb. The C-arm 1 exhibits an adjustable angulation angle α and an adjustable orbital angle φ. The rotational axis is designated A, the associated rotation point is designated D.

In addition to the transmitter 4, 4a, 4b, 4c, in every case a deadman's switch 5, 5a, 5b, 5c is disposed on the image acquisition system 3 as a further operating element. The deadman's switch 5, 5a, 5b, 5c must be operated with a retention force Fh in order to enable the associated transmitter. The deadman's switch 5, 5a, 5b, 5c and the transmitters 4, 4a, 4b, 4c are connected with a control unit 6 via respective lines 8. The control unit 6 is furthermore connected to an electromotor 7 for servo-supported adjustment of the C-arm 1 around the rotation point D. Data identifying the speed v of the C-arm 1 as well as the rotation count n and the armature current Ia of the electromotor 7 are combined in a comparator 9 which is likewise connected with the control unit 6. The position of the C-arm 1 is designated Yc. The control unit 6 additionally has a monitoring unit 10 that detects both a stop of the C-arm 1 at an end position and abnormal operating states. Abnormal operating states are, for example, unexpectedly high acceleration a, or jerky or abrupt movement resistances of the C-arm 1. A deactivation of the electromotor 7 ensues in these cases.

In the exemplary embodiment according to FIG. 1, a first transmitter 4 is fashioned in the form of a rail disposed on the image acquisition system 3, also designated as a servo rail, which in particular exhibits the form of a conventional handgrip. Various exemplary embodiments of further transmitters 4a, 4b, 4b that are disposed on the C-arm 1 or on the x-ray radiator 2 are additionally, as examples shown. For adjustment of the angulation angle α and/or the orbital angle φ, the user requires only one of the transmitters 4, 4a, 4b, 4c (preferably fashioned as a bow-shaped rail) interacting with force and/or displacement transducers (not shown). Each transmitter 4, 4a, 4b, 4c is directly arranged on the C-arm 1 and/or on a part mechanically connected thereto. Actuation of the transmitter 4, 4a, 4b, 4c provides the speed with which the C-arm 1 is adjusted in the actuation direction.

The deadman's switch 5, 5a, 5b, 5c are associated with the transmitter 4, 4a, 4b, 4c. Each of the switches 5, 5a, 5b, 5c is a compact sensor in proximity to the respective transmitter 4, 4a, 4b, 4c and serves to enable the associated transmitter 4, 4a, 4b, 4c in order to prevent an unintentional triggering of an adjustment of the C-arm 1, in particular, adjustment that may create a safety risk to personnel in the vicinity of the apparatus. The transmitter 4, 4a, 4b, 4c can be charged with the operating force Fb in arbitrary directions, and a feedback effect is produced by the controlled operation of the electromotor 7 that conveys to the user the feeling of moving the C-arm 1 with a weight less than its actual weight. The C-arm 1 with the x-ray radiator 2 and the image acquisition system 3 need not be weight-balanced in the manner of a conventional isocentric system. Instead, a weight compensation preferably is foregone in order to keep the total weight low.

The transmitter 4 is fashioned as a sensor membrane disposed directly on the C-arm 1 in the apparatus shown in FIG. 1. This acts as a tactile membrane, which directly detects forces applied on the C-arm 1 by the user, and emits a multi-direction-dependent signal. The transmitter 4 fashioned as a sensor membrane spans wide portions of the externally accessible surface of the C-arm 1, at least in the regions adjacent in the x-ray radiator 2 as well as the image acquisition system 3.

In the exemplary embodiment according to FIG. 3, no sensors are mounted on the surface of the C-arm 1. Instead, forces acting in the suspension 12 of the C-arm 1 are detected by at least one central sensor 11. The central sensor 11 detects forces applied on the C-arm 1 by the user and transduces these into signals for the control unit 6. Virtually the entire C-arm 1, including the x-ray-related components 2,3 connected thereto, act as a single transmitter 4 in this manner. The user can move the C-arm 1 as if it had no servo support but exhibited a lower weight.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray apparatus comprising:

a C-arm;

an x-ray source mounted at a first end of said C-arm and a radiation detector mounted at a second, opposite end of said C-arm;

a motor in driving connection with said C-arm;

a control unit connected to said motor for controlling said motor for servo-supported adjustment of said C-arm through an angulation angle and an orbital angle of said C-arm; and a sensor membrane disposed on and along a circumference of said C-arm for sensing directions and magnitudes of multi-directional forces manually applied to said C-arm by an operator, said sensor membrane being connected to said control unit and supplying a signal thereto, representing said directions and magnitudes, and said control unit operating said motor, substantially simultaneously with the manually applied multi-directional forces and sensing of said directions and magnitudes thereof by said sensor membrane, dependent on the directions and magnitudes of said applied forces to assist the operator in adjusting said C-arm along said directions while said multi-directional forces are being manually applied.

2. An x-ray apparatus as claimed in claim 1 wherein said control unit determines a speed of movement of said C-arm from said directions and magnitudes sensed by said sensor membrane, and operates said motor to assist the operation in adjusting said C-arm at said speed.

3. An x-ray apparatus as claimed in claim 1 wherein said sensor membrane is a part of a servo rail mechanically attached to at least one of said C-arm, said X-ray source, or said radiation detector.

4. An x-ray apparatus as claimed in claim 1 further comprising a deadman's switch connected to said control unit, which must be actuated to enable operation of said sensor membrane.

5. An x-ray apparatus as claimed in claim 1 further comprising a monitoring device for monitoring movement of said C-arm.

* * * * *